(12) United States Patent
Himmler et al.

(10) Patent No.: US 7,638,547 B2
(45) Date of Patent: Dec. 29, 2009

(54) CIS-ALKOXY-SUBSTITUTED SPIROCYCLIC 1H-PYRROLIDINE-2,4-DIONE DERIVATIVES SERVING AS PESTICIDES

(75) Inventors: Thomas Himmler, Odenthal (DE); Reiner Fischer, Monheim (DE); Bernd Gallenkamp, Wuppertal (DE); Hans-Joachim Knops, Monheim (DE); Lubbertus Mulder, Hagen (DE); Reinhard Lantzsch, Wuppertal (DE); Christoph Erdelen, Leichlingen (DE); Angelika Lubos-Erdelen, legal representative, Leichlingen (DE); Jörg Konze, Köln (DE); Ralf Nauen, Langenfeld (DE); Olga Malsam, Rösrath (DE); Christian Arnold, Wachtberg (DE)

(73) Assignee: Bayer CropScience AG, Monheim (DE)

( * ) Notice: Subject to any disclaimer, the term of this patent is extended or adjusted under 35 U.S.C. 154(b) by 718 days.

(21) Appl. No.: 10/520,549

(22) PCT Filed: Jul. 1, 2003

(86) PCT No.: PCT/EP03/06980

§ 371 (c)(1),
(2), (4) Date: Mar. 9, 2006

(87) PCT Pub. No.: WO2004/007448

PCT Pub. Date: Jan. 22, 2004

(65) Prior Publication Data

US 2007/0032539 A1 Feb. 8, 2007

(30) Foreign Application Priority Data

Jul. 11, 2002 (DE) .............................. 102 31 333

(51) Int. Cl.
*A01N 43/38* (2006.01)
*C07D 209/96* (2006.01)
(52) U.S. Cl. ...................................... 514/409; 548/408
(58) Field of Classification Search ........................ None
See application file for complete search history.

(56) References Cited

U.S. PATENT DOCUMENTS

| | | | |
|---|---|---|---|
| 5,462,913 A | 10/1995 | Fischer et al. ................ 504/138 |
| 5,622,917 A | 4/1997 | Fischer et al. ................ 504/283 |
| 5,677,449 A | 10/1997 | Fischer et al. ................ 544/165 |
| 5,830,826 A | 11/1998 | Fischer et al. ................ 504/195 |
| 5,847,211 A | 12/1998 | Fischer et al. ................ 564/123 |
| 5,994,274 A | 11/1999 | Fischer et al. ................ 504/282 |
| 6,110,872 A | 8/2000 | Lieb et al. .................... 504/284 |
| 6,114,374 A * | 9/2000 | Lieb et al. .................... 514/424 |
| 6,140,358 A | 10/2000 | Lieb et al. .................... 514/425 |
| 6,172,255 B1 | 1/2001 | Fischer et al. ................. 560/24 |
| 6,251,830 B1 | 6/2001 | Fischer et al. ................ 504/251 |
| 6,271,180 B2 | 8/2001 | Lieb et al. .................... 504/292 |
| 6,316,486 B1 | 11/2001 | Lieb et al. .................... 514/411 |
| 6,358,887 B1 | 3/2002 | Fischer et al. ................ 504/284 |
| 6,380,246 B1 | 4/2002 | Lieb et al. .................... 514/462 |
| 6,388,123 B1 | 5/2002 | Lieb et al. ..................... 560/76 |
| 6,417,370 B1 | 7/2002 | Lieb et al. .................... 548/408 |
| 6,451,843 B1 | 9/2002 | Lieb et al. .................... 514/422 |
| 6,458,965 B1 | 10/2002 | Lieb et al. .................... 548/408 |
| 6,469,196 B2 | 10/2002 | Fischer et al. ................ 560/105 |
| 6,472,419 B1 | 10/2002 | Fischer et al. ................ 514/425 |
| 6,486,343 B1 | 11/2002 | Lieb et al. ..................... 560/39 |
| 6,511,942 B1 | 1/2003 | Lieb et al. .................... 504/299 |
| 6,693,092 B2 | 2/2004 | Lieb et al. .................... 514/183 |
| 6,716,832 B2 | 4/2004 | Lieb et al. .................... 514/183 |
| 6,746,990 B2 | 6/2004 | Fischer et al. ................ 504/299 |
| 6,759,548 B2 | 7/2004 | Fischer et al. ................. 560/81 |
| 6,806,264 B2 | 10/2004 | Lieb et al. .................... 514/183 |
| 6,861,391 B1 | 3/2005 | Fischer et al. ................ 504/283 |
| 2001/0004629 A1 | 6/2001 | Lieb et al. .................... 504/292 |
| 2002/0022575 A1 | 2/2002 | Fischer et al. ................ 504/221 |
| 2002/0188136 A1 | 12/2002 | Lieb et al. .................. 548/368.4 |
| 2003/0045432 A1 | 3/2003 | Fischer et al. ................ 504/221 |
| 2003/0073851 A1 | 4/2003 | Lieb et al. .................. 548/366.4 |
| 2003/0096806 A1 | 5/2003 | Lieb et al. ............... 514/212.01 |
| 2003/0144504 A1 | 7/2003 | Fischer et al. ................. 544/54 |
| 2003/0171219 A1 | 9/2003 | Lieb et al. .................... 504/221 |
| 2003/0199572 A1 | 10/2003 | Lieb et al. .................... 514/451 |

(Continued)

FOREIGN PATENT DOCUMENTS

JP 2002-205984 7/2002

(Continued)

OTHER PUBLICATIONS

Chem. Reviews, 52, (month unavailable) 1953, pp. 237-416, Norman O.V. Sonntag, "The Reactions of Aliphatic Acid Chlorides".

(Continued)

*Primary Examiner*—Kamal A Saeed
(74) *Attorney, Agent, or Firm*—Richard E. L. Henderson

(57) ABSTRACT

The invention relates to novel cis-alkoxy-substituted spirocyclic 1H-pyrrolidine-2,4-dione derivatives of the formula (I)

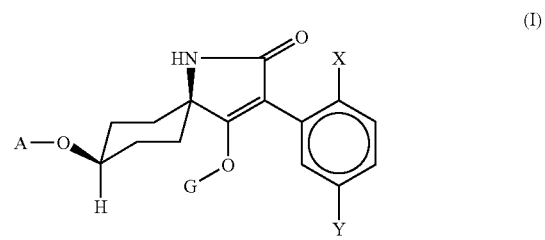

in which A, G, X and Y are as defined in the disclosure, to a plurality of processes for their preparation and to their use as pesticides.

5 Claims, No Drawings

U.S. PATENT DOCUMENTS

| | | | |
|---|---|---|---|
| 2004/0019061 A1 | 1/2004 | Fischer et al. | 514/256 |
| 2004/0039223 A1 | 2/2004 | Himmler et al. | 560/125 |
| 2004/0127365 A1 | 7/2004 | Lieb et al. | 504/282 |
| 2004/0167031 A1 | 8/2004 | Lieb et al. | 504/308 |

FOREIGN PATENT DOCUMENTS

| | | |
|---|---|---|
| WO | 98/05638 | 2/1998 |
| WO | 01/74770 | 10/2001 |
| WO | 02/37963 | 5/2002 |
| WO | 03/029213 | 4/2003 |

OTHER PUBLICATIONS

Indian J. Chem., vol. 6, Jul. 1968, pp. 341-345, Bhabatosh Bhattacharya, "Isoquinoline Derivatives: Part XVIII-Formation of I-Alkyl-(or alkaryl or aryl)-3-methyl-7-chloro-(or 5-chloro)-Isoquinolines".

Schotten-Baumann, Organikum, VEB (month unavailable) 1977, p. 505-507, "Reaktionen von Carbonsäuren und Carbonsäurederivaten mit Basen".

Chem. Ind., 37, (month unavailable) 1985, pp. 730-732, Harry R. Ungerer, "Schiffsfarben—eine Spezialität der seenahen Lackindustrie".

* cited by examiner

CIS-ALKOXY-SUBSTITUTED SPIROCYCLIC 1H-PYRROLIDINE-2,4-DIONE DERIVATIVES SERVING AS PESTICIDES

The present patent application has been filed under 35 U.S.C. 371 as a national stage application of PCT/EP2003/006980, filed Jul. 1, 2003, which was published in German as International Patent Publication WO 2004/007448 on Jan. 22, 2004, and is entitled to the right of priority of German Patent Application 10231333.4, filed Jul. 11, 2002.

The present invention relates to novel cis-alkoxy-substituted spirocyclic 1H-pyrrolidine-2,4-dione derivatives, to a plurality of processes for their preparation and to their use as pesticides.

Alkoxy-substituted spirocyclic 1H-pyrrolidine-2,4-dione derivatives having acaricidal, insecticidal and herbicidal action are known:

EP-A 596 298, WO 95/26954, WO 95/20572, EP-A 668 267, WO 96/25395, WO 96/35664, WO 97/01535, WO 97/02243, WO 97/36868, WO 98/05638, WO 99/43649, WO 99/48869, WO 99/55673, WO 01/23354, WO 01/74770.

Owing to the preparation processes, the known compounds are obtained in the form of cis/trans isomer mixtures with varying cis/trans ratios.

This invention now provides novel compounds of the formula (I)

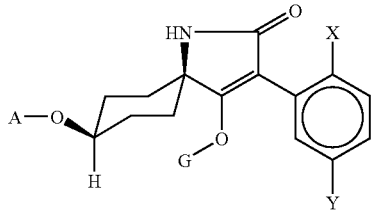

(I)

in which
X represents alkyl, halogen, alkoxy, haloalkyl or haloalkoxy,
Y represents hydrogen, alkyl, alkoxy, halogen, haloalkyl or haloalkoxy, where only one of the radicals X and Y may represent haloalkyl or haloalkoxy,
A represents $C_1$-$C_6$-alkyl,
G represents hydrogen (a) or represents one of the groups

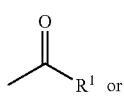

(b)

or

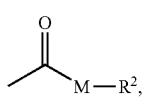

(c)

in which
M represents oxygen or sulphur,
$R^1$ represents in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl or poly-$C_1$-$C_8$-alkoxy-$C_1$-$C_8$-alkyl or represents optionally halogen-, $C_1$-$C_6$-alkyl- or $C_1$-$C_6$-alkoxy-substituted $C_3$-$C_8$-cycloalkyl in which optionally one or two not directly adjacent methylene groups are replaced by oxygen and/or sulphur, represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl-substituted phenyl or represents thienyl,
$R^2$ represents in each case optionally halogen-substituted $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl,
represents optionally halogen-, $C_1$-$C_6$-alkyl- or $C_1$-$C_6$-alkoxy-substituted $C_3$-$C_8$-cycloalkyl or
represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl.

Including the different meanings (a), (b) and (c) of group G, the following principal structures (I-a) to (I-c) result (cis-isomer):

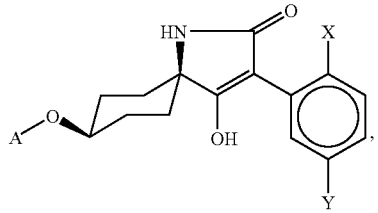

(I-a)

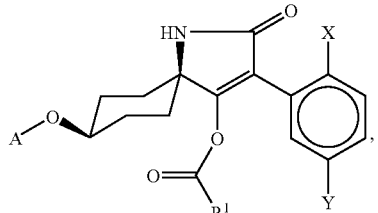

(I-b)

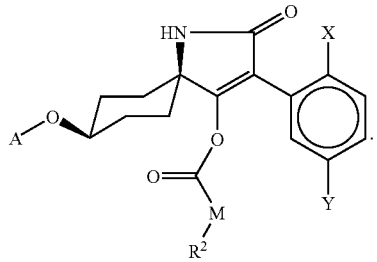

(I-c)

Furthermore, it has been found that the novel compounds of the formula (I) are obtained by one of the processes described below:

(A) compounds of the formula (I-1-a)

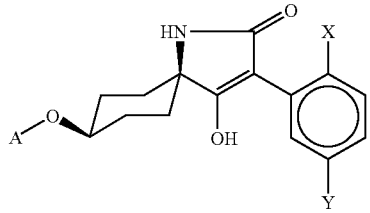

(I-1-a)

in which
A, X and Y are as defined above
are obtained when
compounds of the formula (II)

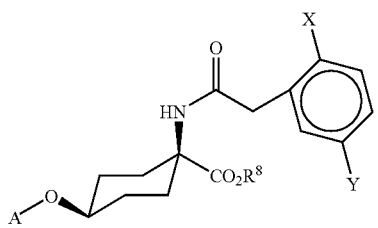

(II)

in which

A, X and Y are as defined above and $R^8$ represents alkyl (preferably $C_1$-$C_6$-alkyl)

are condensed intramolecularly in the presence of a diluent and in the presence of a base.

Moreover, it has been found (B) that the compounds of the formula (I-b) shown above in which A, $R^1$, X and Y are as defined above are obtained when compounds of the formula (I-a) shown above in which A, X and Y are as defined above are reacted α) with acid halides of the formula (III)

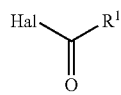

(III)

in which $R^1$ is as defined above and

Hal represents halogen (in particular chlorine or bromine)

or

β) with carboxylic anhydrides of the formula (IV)

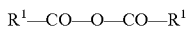

(IV)

in which $R^1$ is as defined above, if appropriate in the presence of a diluent and if appropriate in the presence of an acid binder;

(C) that the compounds of the formula (I-c) shown above in which A, $R^2$, M, X and Y are as defined above are obtained when compounds of the formula (I-a) shown above in which A, X and Y are as defined above are in each case reacted with chloroformic esters or chloroformic thioesters of the formula (V)

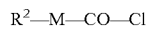

(V)

in which $R^2$ and M are as defined above, if appropriate in the presence of a diluent and if appropriate in the presence of an acid binder;

(D) that the compounds of the formulae (I-a) to (I-c) shown above are obtained when cis/trans isomer mixtures of the formulae (I-a') to (I-c'), known, for example, from WO 98/05638 or WO 01/74770,

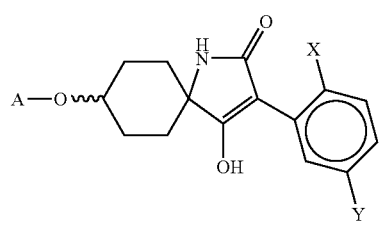

(I-a')

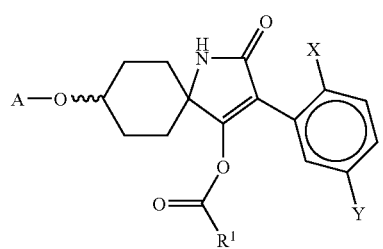

(I-b')

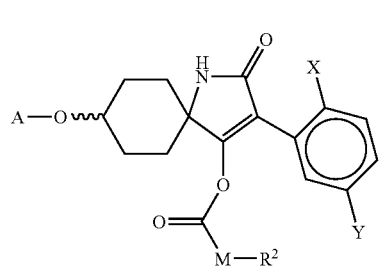

(I-c')

in which

A, X, Y, M, $R^1$ and $R^2$ are as defined above, are separated using physical separation processes, such as, for example, by column chromatography or fractional crystallization.

(E) Furthermore, it has been found that compounds of the formula (I-a) are obtained when compounds of the formulae (I-b) or (I-c) in which A, M, X, Y, $R^1$ and $R^2$ are as defined above are hydrolysed, for example with aqueous bases, and then acidified.

Furthermore, it has been found that the novel compounds of the formula (I) have good pesticidal action, preferably insecticidal and/or acaricidal action, and are furthermore frequently highly compatible with plants, in particular with crop plants.

The formula (I) provides a general definition of the compounds according to the invention. Preferred substituents or ranges of the radicals listed in the formulae given above and below are illustrated below:

X preferably represents chlorine, bromine, methyl, ethyl, propyl, trifluoromethyl, methoxy, difluoromethoxy or trifluoromethoxy, Y preferably represents hydrogen, chlorine, bromine, methoxy, methyl, ethyl, propyl, trifluoromethyl or trifluoromethoxy, where only one of the radicals X and Y may represent trifluoromethyl, difluoromethoxy or trifluoromethoxy, A preferably represents $C_1$-$C_6$-alkyl, G preferably represents hydrogen (a) or represents one of the groups

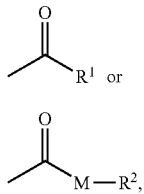

(b)

(c)

in which
M represents oxygen or sulphur,
R$^1$ preferably represents C$_1$-C$_{16}$-alkyl, C$_2$-C$_{16}$-alkenyl, C$_1$-C$_6$-alkoxy-C$_1$-C$_6$-alkyl, C$_1$-C$_6$-alkylthio-C$_1$-C$_6$-alkyl or poly-C$_1$-C$_6$-alkoxy-C$_1$-C$_6$-alkyl, each of which is optionally mono- to trisubstituted by fluorine or chlorine, or represents C$_3$-C$_7$-cycloalkyl which is optionally mono- or disubstituted by fluorine, chlorine, C$_1$-C$_5$-alkyl or C$_1$-C$_5$-alkoxy and in which optionally one or two not directly adjacent methylene groups are replaced by oxygen and/or sulphur,
represents phenyl which is optionally mono- to trisubstituted by fluorine, chlorine, bromine, cyano, nitro, C$_1$-C$_4$-alkyl, C$_1$-C$_4$-alkoxy, C$_1$-C$_3$-haloalkyl, C$_1$-C$_3$-haloalkoxy, C$_1$-C$_4$-alkylthio or C$_1$-C$_4$-alkylsulphonyl or represents thienyl,
R$^2$ particularly preferably represents C$_1$-C$_{16}$-alkyl, C$_2$-C$_{16}$-alkenyl, C$_1$-C$_6$-alkoxy-C$_2$-C$_6$-alkyl or poly-C$_1$-C$_6$-alkoxy-C$_2$-C$_6$-alkyl, each of which is optionally mono- to trisubstituted by fluorine or chlorine,
represents C$_3$-C$_7$-cycloalkyl which is optionally mono- or disubstituted by fluorine, chlorine, C$_1$-C$_4$-alkyl or C$_1$-C$_4$-alkoxy or
represents phenyl or benzyl, each of which is optionally mono- or disubstituted by fluorine, chlorine, bromine, cyano, nitro, C$_1$-C$_4$-alkyl, C$_1$-C$_3$-alkoxy, C$_1$-C$_3$-haloalkyl or C$_1$-C$_3$-haloalkoxy.
X particularly preferably represents chlorine, bromine, methyl, ethyl, methoxy, trifluoromethyl, trifluoromethoxy or difluoromethoxy,
Y particularly preferably represents chlorine, bromine, methyl, ethyl, propyl, methoxy, trifluoromethyl or trifluoromethoxy,
where only one of the radicals X and Y may represent trifluoromethyl, trifluoromethoxy or difluoromethoxy,
A particularly preferably represents C$_1$-C$_4$-alkyl,
G very particularly preferably represents hydrogen (a) or represents one of the groups

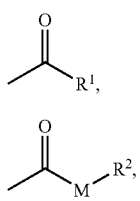

(b)

(c)

in which
M represents oxygen or sulphur,
R$^1$ particularly preferably represents C$_1$-C$_8$-alkyl, C$_2$-C$_8$-alkenyl, C$_1$-C$_2$-alkoxy-C$_1$-C$_2$-alkyl, C$_1$-C$_2$-alkylthio-C$_1$-C$_2$-alkyl, each of which is optionally mono- to trisubstituted by fluorine or chlorine, or represents C$_3$-C$_6$-cycloalkyl which is optionally mono- or disubstituted by fluorine, chlorine, methyl or methoxy and in which optionally one methylene group is replaced by oxygen and/or sulphur,
represents phenyl which is optionally mono- or disubstituted by fluorine, chlorine, bromine, cyano, nitro, methyl, methoxy, trifluoromethyl or trifluoromethoxy or represents thienyl,
R$^2$ particularly preferably represents C$_1$-C$_8$-alkyl, C$_2$-C$_8$-alkenyl or C$_1$-C$_4$-alkoxy-C$_2$-C$_3$-alkyl, represents C$_5$-C$_6$-cycloalkyl,
represents phenyl or benzyl, each of which is monosubstituted by fluorine, chlorine, cyano, nitro, methyl, methoxy, trifluoromethyl or trifluoromethoxy.
X very particularly preferably represents chlorine, bromine, methyl or trifluoromethyl, (especially chlorine, bromine or methyl),
Y very particularly preferably represents chlorine, bromine or methyl, (especially methyl),
A very particularly preferably represents methyl, ethyl, propyl, butyl or isobutyl, (especially methyl or ethyl),
G very particularly preferably represents hydrogen (a) or represents one of the groups

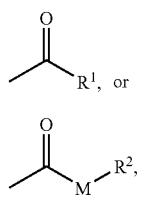

(b)

(c)

in which
M represents oxygen or sulphur, (especially oxygen),
R$^1$ very particularly preferably represents C$_1$-C$_6$-alkyl, C$_2$-C$_6$-alkenyl, C$_1$-C$_2$-alkoxy-C$_1$-C$_2$-alkyl, C$_1$-C$_2$-alkylthio-C$_1$-C$_2$-alkyl, represents cyclopropyl, cyclopentyl or cyclohexyl, each of which is optionally monosubstituted by fluorine, chlorine, methyl or methoxy,
represents phenyl which is optionally monosubstituted by fluorine, chlorine, bromine, cyano, nitro, methyl, methoxy, trifluoromethyl or trifluoromethoxy or represents thienyl,
R$^2$ very particularly preferably represents C$_1$-C$_8$-alkyl, C$_2$-C$_6$-alkenyl or C$_1$-C$_3$-alkoxy-C$_2$-C$_3$-alkyl,
represents cyclopentyl or cyclohexyl
or represents phenyl or benzyl, each of which is optionally monosubstituted by fluorine, chlorine, cyano, nitro, methyl, methoxy, trifluoromethyl or trifluoromethoxy.

The general or preferred radical definitions or explanations given above can be combined with one another as desired, i.e. including any combinations between the respective ranges and preferred ranges. They apply both to the end products and, correspondingly, to the precursors and intermediates.

Preference according to the invention is given to the compounds of the formula (I) which contain a combination of the meanings given above as being preferred (preferable).

Particular preference according to the invention is given to the compounds of the formula (I) which contain a combination of the meanings given above as being particularly preferred.

Very particular preference according to the invention is given to the compounds of the formula (I) which contain a combination of the meanings given above as being very particularly preferred.

Saturated or unsaturated hydrocarbon radicals, such as alkyl or alkenyl, can in each case be straight-chain or branched as far as this is possible, including in combination with heteroatoms, such as, for example, in alkoxy.

Optionally substituted radicals can be mono- or polysubstituted, where, in the case of polysubstitution, the substituents can be identical or different.

In addition to the compounds mentioned in the Preparation Examples, particular mention may be made of the following compounds of the formula (I-a):

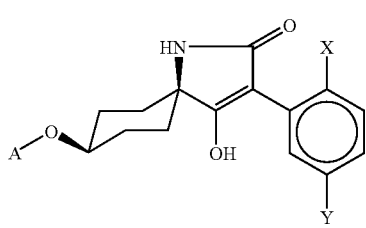
(I-a)

TABLE 1

A = CH₃

| X | Y |
|---|---|
| CH₃ | CH₃ |
| Cl | CH₃ |
| CH₃ | Cl |
| Br | CH₃ |
| CH₃ | Br |

TABLE 2

A = C₂H₅

| X | Y |
|---|---|
| CH₃ | CH₃ |
| Cl | CH₃ |
| CH₃ | Cl |
| Br | CH₃ |
| CH₃ | Br |

TABLE 3

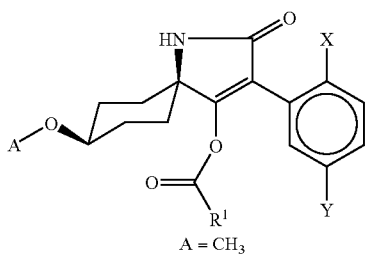
(I-b)

A = CH₃

| X | Y | R¹ |
|---|---|---|
| CH₃ | CH₃ | CH₃ |
| CH₃ | CH₃ | C₂H₅ |
| CH₃ | CH₃ | C₃H₇ |
| CH₃ | CH₃ | i-C₃H₇ |
| CH₃ | CH₃ | C₄H₉ |
| CH₃ | CH₃ | i-C₄H₉ |
| CH₃ | CH₃ | s-C₄H₉ |
| CH₃ | CH₃ | t-C₄H₉ |
| CH₃ | CH₃ | CH₂-t-C₄H₉ |
| CH₃ | CH₃ | c-C₃H₅ |
| CH₃ | CH₃ | H₅C₂—O—CH₂ |
| CH₃ | CH₃ | 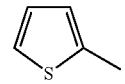 |
| CH₃ | CH₃ | |

TABLE 4

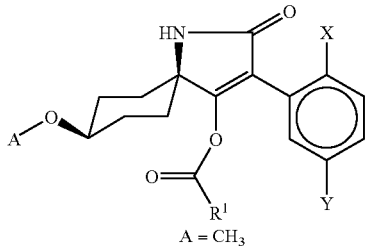
(I-b)

A = CH₃

| X | Y | R¹ |
|---|---|---|
| Br | CH₃ | CH₃ |
| Br | CH₃ | C₂H₅ |
| Br | CH₃ | C₃H₇ |
| Br | CH₃ | i-C₃H₇ |
| Br | CH₃ | C₄H₉ |
| Br | CH₃ | i-C₄H₉ |
| Br | CH₃ | s-C₄H₉ |
| Br | CH₃ | t-C₄H₉ |
| Br | CH₃ | CH₂-t-C₄H₉ |
| Br | CH₃ | c-C₃H₅ |
| Br | CH₃ | H₅C₂—O—CH₂ |
| Br | CH₃ | |
| Br | CH₃ | 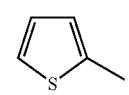 |

TABLE 5

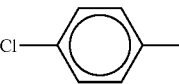

(I-b)

A = CH₃

| X | Y | R¹ |
|---|---|---|
| CH₃ | Br | CH₃ |
| CH₃ | Br | C₂H₅ |
| CH₃ | Br | C₃H₇ |
| CH₃ | Br | i-C₃H₇ |
| CH₃ | Br | C₄H₉ |
| CH₃ | Br | i-C₄H₉ |
| CH₃ | Br | s-C₄H₉ |
| CH₃ | Br | t-C₄H₉ |
| CH₃ | Br | CH₂-t-C₄H₉ |
| CH₃ | Br | c-C₃H₅ |
| CH₃ | Br | H₅C₂—O—CH₂ |
| CH₃ | Br | 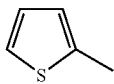 |
| CH₃ | Br |  |

TABLE 6

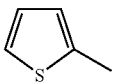

(I-b)

A = CH₃

| X | Y | R¹ |
|---|---|---|
| Cl | CH₃ | CH₃ |
| Cl | CH₃ | C₂H₅ |
| Cl | CH₃ | C₃H₇ |
| Cl | CH₃ | i-C₃H₇ |
| Cl | CH₃ | C₄H₉ |
| Cl | CH₃ | i-C₄H₉ |
| Cl | CH₃ | s-C₄H₉ |
| Cl | CH₃ | t-C₄H₉ |
| Cl | CH₃ | CH₂-t-C₄H₉ |
| Cl | CH₃ | c-C₃H₅ |
| Cl | CH₃ | H₅C₂—O—CH₂ |
| Cl | CH₃ | 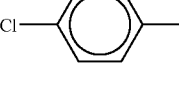 |
| Cl | CH₃ | 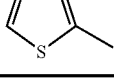 |

TABLE 7

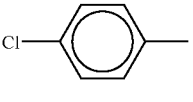

(I-b)

A = CH₃

| X | Y | R¹ |
|---|---|---|
| CH₃ | Cl | CH₃ |
| CH₃ | Cl | C₂H₅ |
| CH₃ | Cl | C₃H₇ |
| CH₃ | Cl | i-C₃H₇ |
| CH₃ | Cl | C₄H₉ |
| CH₃ | Cl | i-C₄H₉ |
| CH₃ | Cl | s-C₄H₉ |
| CH₃ | Cl | t-C₄H₉ |
| CH₃ | Cl | CH₂-t-C₄H₉ |
| CH₃ | Cl | c-C₃H₅ |
| CH₃ | Cl | H₅C₂—O—CH₂ |
| CH₃ | Cl | 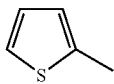 |
| CH₃ | Cl |  |

TABLE 8

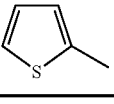

(I-b)

A = C₂H₅

| X | Y | R¹ |
|---|---|---|
| CH₃ | CH₃ | CH₃ |
| CH₃ | CH₃ | C₂H₅ |
| CH₃ | CH₃ | C₃H₇ |
| CH₃ | CH₃ | i-C₃H₇ |
| CH₃ | CH₃ | C₄H₉ |
| CH₃ | CH₃ | i-C₄H₉ |
| CH₃ | CH₃ | s-C₄H₉ |
| CH₃ | CH₃ | t-C₄H₉ |
| CH₃ | CH₃ | CH₂-t-C₄H₉ |
| CH₃ | CH₃ | c-C₃H₅ |
| CH₃ | CH₃ | H₅C₂—O—CH₂ |
| CH₃ | CH₃ | 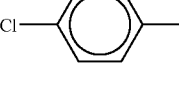 |
| CH₃ | CH₃ | 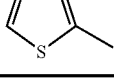 |

TABLE 9

(I-b)

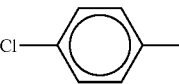

A = C$_2$H$_5$

| X | Y | R$^1$ |
|---|---|---|
| Br | CH$_3$ | CH$_3$ |
| Br | CH$_3$ | C$_2$H$_5$ |
| Br | CH$_3$ | C$_3$H$_7$ |
| Br | CH$_3$ | i-C$_3$H$_7$ |
| Br | CH$_3$ | C$_4$H$_9$ |
| Br | CH$_3$ | i-C$_4$H$_9$ |
| Br | CH$_3$ | s-C$_4$H$_9$ |
| Br | CH$_3$ | t-C$_4$H$_9$ |
| Br | CH$_3$ | CH$_2$-t-C$_4$H$_9$ |
| Br | CH$_3$ | c-C$_3$H$_5$ |
| Br | CH$_3$ | H$_5$C$_2$—O—CH$_2$ |
| Br | CH$_3$ | 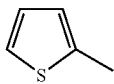 |
| Br | CH$_3$ | 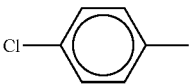 |

TABLE 10

(I-b)

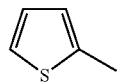

A = C$_2$H$_5$

| X | Y | R$^1$ |
|---|---|---|
| CH$_3$ | Br | CH$_3$ |
| CH$_3$ | Br | C$_2$H$_5$ |
| CH$_3$ | Br | C$_3$H$_7$ |
| CH$_3$ | Br | i-C$_3$H$_7$ |
| CH$_3$ | Br | C$_4$H$_9$ |
| CH$_3$ | Br | i-C$_4$H$_9$ |
| CH$_3$ | Br | s-C$_4$H$_9$ |
| CH$_3$ | Br | t-C$_4$H$_9$ |
| CH$_3$ | Br | CH$_2$-t-C$_4$H$_9$ |
| CH$_3$ | Br | c-C$_3$H$_5$ |
| CH$_3$ | Br | H$_5$C$_2$—O—CH$_2$ |
| CH$_3$ | Br | 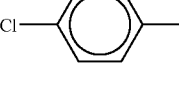 |
| CH$_3$ | Br | 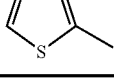 |

TABLE 11

(I-b)

A = C$_2$H$_5$

| X | Y | R$^1$ |
|---|---|---|
| Cl | CH$_3$ | CH$_3$ |
| Cl | CH$_3$ | C$_2$H$_5$ |
| Cl | CH$_3$ | C$_3$H$_7$ |
| Cl | CH$_3$ | i-C$_3$H$_7$ |
| Cl | CH$_3$ | C$_4$H$_9$ |
| Cl | CH$_3$ | i-C$_4$H$_9$ |
| Cl | CH$_3$ | s-C$_4$H$_9$ |
| Cl | CH$_3$ | t-C$_4$H$_9$ |
| Cl | CH$_3$ | CH$_2$-t-C$_4$H$_9$ |
| Cl | CH$_3$ | c-C$_3$H$_5$ |
| Cl | CH$_3$ | H$_5$C$_2$—O—CH$_2$ |
| Cl | CH$_3$ | |
| Cl | CH$_3$ | |

TABLE 12

(I-b)

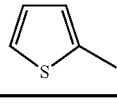

A = C$_2$H$_5$

| X | Y | R$^1$ |
|---|---|---|
| CH$_3$ | Cl | CH$_3$ |
| CH$_3$ | Cl | C$_2$H$_5$ |
| CH$_3$ | Cl | C$_3$H$_7$ |
| CH$_3$ | Cl | i-C$_3$H$_7$ |
| CH$_3$ | Cl | C$_4$H$_9$ |
| CH$_3$ | Cl | i-C$_4$H$_9$ |
| CH$_3$ | Cl | s-C$_4$H$_9$ |
| CH$_3$ | Cl | t-C$_4$H$_9$ |
| CH$_3$ | Cl | CH$_2$-t-C$_4$H$_9$ |
| CH$_3$ | Cl | c-C$_3$H$_5$ |
| CH$_3$ | Cl | H$_5$C$_2$—O—CH$_2$ |
| CH$_3$ | Cl | |
| CH$_3$ | Cl | |

TABLE 13

(I-c)

A = CH₃   M = O

| X | Y | R² |
|---|---|----|
| CH₃ | CH₃ | CH₃ |
| CH₃ | CH₃ | C₂H₅ |
| CH₃ | CH₃ | C₃H₇ |
| CH₃ | CH₃ | i-C₃H₇ |
| CH₃ | CH₃ | C₄H₉ |
| CH₃ | CH₃ | i-C₄H₉ |
| CH₃ | CH₃ | s-C₄H₉ |
| CH₃ | CH₃ | t-C₄H₉ |
| CH₃ | CH₃ | CH₂-t-C₄H₉ |
| CH₃ | CH₃ | CH₂—C₆H₅ |
| CH₃ | CH₃ | C₆H₅ |

TABLE 14

(I-c)

A = CH₃   M = O

| X | Y | R² |
|---|---|----|
| Br | CH₃ | CH₃ |
| Br | CH₃ | C₂H₅ |
| Br | CH₃ | C₃H₇ |
| Br | CH₃ | i-C₃H₇ |
| Br | CH₃ | C₄H₉ |
| Br | CH₃ | i-C₄H₉ |
| Br | CH₃ | s-C₄H₉ |
| Br | CH₃ | t-C₄H₉ |
| Br | CH₃ | CH₂-t-C₄H₉ |
| Br | CH₃ | CH₂—C₆H₅ |
| Br | CH₃ | C₆H₅ |

TABLE 15

(I-c)

A = CH₃   M = O

| X | Y | R² |
|---|---|----|
| CH₃ | Br | CH₃ |
| CH₃ | Br | C₂H₅ |
| CH₃ | Br | C₃H₇ |
| CH₃ | Br | i-C₃H₇ |
| CH₃ | Br | C₄H₉ |
| CH₃ | Br | i-C₄H₉ |
| CH₃ | Br | s-C₄H₉ |
| CH₃ | Br | t-C₄H₉ |
| CH₃ | Br | CH₂-t-C₄H₉ |
| CH₃ | Br | CH₂—C₆H₅ |
| CH₃ | Br | C₆H₅ |

TABLE 16

(I-c)

A = CH₃   M = O

| X | Y | R² |
|---|---|----|
| Cl | CH₃ | CH₃ |
| Cl | CH₃ | C₂H₅ |
| Cl | CH₃ | C₃H₇ |
| Cl | CH₃ | i-C₃H₇ |
| Cl | CH₃ | C₄H₉ |
| Cl | CH₃ | i-C₄H₉ |
| Cl | CH₃ | s-C₄H₉ |
| Cl | CH₃ | t-C₄H₉ |
| Cl | CH₃ | CH₂-t-C₄H₉ |
| Cl | CH₃ | CH₂—C₆H₅ |
| Cl | CH₃ | C₆H₅ |

TABLE 17

(I-c)

A = CH₃     M = O

| X | Y | R² |
|---|---|---|
| CH₃ | Cl | CH₃ |
| CH₃ | Cl | C₂H₅ |
| CH₃ | Cl | C₃H₇ |
| CH₃ | Cl | i-C₃H₇ |
| CH₃ | Cl | C₄H₉ |
| CH₃ | Cl | i-C₄H₉ |
| CH₃ | Cl | s-C₄H₉ |
| CH₃ | Cl | t-C₄H₉ |
| CH₃ | Cl | CH₂-t-C₄H₉ |
| CH₃ | Cl | CH₂—C₆H₅ |
| CH₃ | Cl | C₆H₅ |

TABLE 18

(I-c)

A = C₂H₅     M = O

| X | Y | R² |
|---|---|---|
| CH₃ | CH₃ | CH₃ |
| CH₃ | CH₃ | C₂H₅ |
| CH₃ | CH₃ | C₃H₇ |
| CH₃ | CH₃ | i-C₃H₇ |
| CH₃ | CH₃ | C₄H₉ |
| CH₃ | CH₃ | i-C₄H₉ |
| CH₃ | CH₃ | s-C₄H₉ |
| CH₃ | CH₃ | t-C₄H₉ |
| CH₃ | CH₃ | CH₂-t-C₄H₉ |
| CH₃ | CH₃ | CH₂—C₆H₅ |
| CH₃ | CH₃ | C₆H₅ |

TABLE 19

(I-c)

A = C₂H₅     M = O

| X | Y | R² |
|---|---|---|
| Br | CH₃ | CH₃ |
| Br | CH₃ | C₂H₅ |
| Br | CH₃ | C₃H₇ |
| Br | CH₃ | i-C₃H₇ |
| Br | CH₃ | C₄H₉ |
| Br | CH₃ | i-C₄H₉ |
| Br | CH₃ | s-C₄H₉ |
| Br | CH₃ | t-C₄H₉ |
| Br | CH₃ | CH₂-t-C₄H₉ |
| Br | CH₃ | CH₂—C₆H₅ |
| Br | CH₃ | C₆H₅ |

TABLE 20

(I-c)

A = C₂H₅     M = O

| X | Y | R² |
|---|---|---|
| CH₃ | Br | CH₃ |
| CH₃ | Br | C₂H₅ |
| CH₃ | Br | C₃H₇ |
| CH₃ | Br | i-C₃H₇ |
| CH₃ | Br | C₄H₉ |
| CH₃ | Br | i-C₄H₉ |
| CH₃ | Br | s-C₄H₉ |
| CH₃ | Br | t-C₄H₉ |
| CH₃ | Br | CH₂-t-C₄H₉ |
| CH₃ | Br | CH₂—C₆H₅ |
| CH₃ | Br | C₆H₅ |

TABLE 21

(I-c)

A = C$_2$H$_5$    M = O

| X | Y | R$^2$ |
|---|---|---|
| Cl | CH$_3$ | CH$_3$ |
| Cl | CH$_3$ | C$_2$H$_5$ |
| Cl | CH$_3$ | C$_3$H$_7$ |
| Cl | CH$_3$ | i-C$_3$H$_7$ |
| Cl | CH$_3$ | C$_4$H$_9$ |
| Cl | CH$_3$ | i-C$_4$H$_9$ |
| Cl | CH$_3$ | s-C$_4$H$_9$ |
| Cl | CH$_3$ | t-C$_4$H$_9$ |
| Cl | CH$_3$ | CH$_2$-t-C$_4$H$_9$ |
| Cl | CH$_3$ | CH$_2$—C$_6$H$_5$ |
| Cl | CH$_3$ | C$_6$H$_5$ |

TABLE 22

(I-c)

A = C$_2$H$_5$    M = O

| X | Y | R$^2$ |
|---|---|---|
| CH$_3$ | Cl | CH$_3$ |
| CH$_3$ | Cl | C$_2$H$_5$ |
| CH$_3$ | Cl | C$_3$H$_7$ |
| CH$_3$ | Cl | i-C$_3$H$_7$ |
| CH$_3$ | Cl | C$_4$H$_9$ |
| CH$_3$ | Cl | i-C$_4$H$_9$ |
| CH$_3$ | Cl | s-C$_4$H$_9$ |
| CH$_3$ | Cl | t-C$_4$H$_9$ |
| CH$_3$ | Cl | CH$_2$-t-C$_4$H$_9$ |
| CH$_3$ | Cl | CH$_2$—C$_6$H$_5$ |
| CH$_3$ | Cl | C$_6$H$_5$ |

TABLE 23

(I-c)

A = CH$_3$    M = S

| X | Y | R$^2$ |
|---|---|---|
| CH$_3$ | CH$_3$ | CH$_3$ |
| CH$_3$ | CH$_3$ | C$_2$H$_5$ |
| CH$_3$ | CH$_3$ | C$_3$H$_7$ |
| CH$_3$ | CH$_3$ | i-C$_3$H$_7$ |
| CH$_3$ | CH$_3$ | C$_4$H$_9$ |
| CH$_3$ | CH$_3$ | i-C$_4$H$_9$ |
| CH$_3$ | CH$_3$ | s-C$_4$H$_9$ |
| CH$_3$ | CH$_3$ | t-C$_4$H$_9$ |
| CH$_3$ | CH$_3$ | CH$_2$-t-C$_4$H$_9$ |
| CH$_3$ | CH$_3$ | CH$_2$—C$_6$H$_5$ |
| CH$_3$ | CH$_3$ | C$_6$H$_5$ |

TABLE 24

(I-c)

A = CH$_3$    M = S

| X | Y | R$^2$ |
|---|---|---|
| Br | CH$_3$ | CH$_3$ |
| Br | CH$_3$ | C$_2$H$_5$ |
| Br | CH$_3$ | C$_3$H$_7$ |
| Br | CH$_3$ | i-C$_3$H$_7$ |
| Br | CH$_3$ | C$_4$H$_9$ |
| Br | CH$_3$ | i-C$_4$H$_9$ |
| Br | CH$_3$ | s-C$_4$H$_9$ |
| Br | CH$_3$ | t-C$_4$H$_9$ |
| Br | CH$_3$ | CH$_2$-t-C$_4$H$_9$ |
| Br | CH$_3$ | CH$_2$—C$_6$H$_5$ |
| Br | CH$_3$ | C$_6$H$_5$ |

TABLE 25

(I-c)

A = CH₃    M = S

| X | Y | R² |
|---|---|---|
| CH₃ | Br | CH₃ |
| CH₃ | Br | C₂H₅ |
| CH₃ | Br | C₃H₇ |
| CH₃ | Br | i-C₃H₇ |
| CH₃ | Br | C₄H₉ |
| CH₃ | Br | i-C₄H₉ |
| CH₃ | Br | s-C₄H₉ |
| CH₃ | Br | t-C₄H₉ |
| CH₃ | Br | CH₂-t-C₄H₉ |
| CH₃ | Br | CH₂—C₆H₅ |
| CH₃ | Br | C₆H₅ |

TABLE 26

(I-c)

A = CH₃    M = S

| X | Y | R² |
|---|---|---|
| Cl | CH₃ | CH₃ |
| Cl | CH₃ | C₂H₅ |
| Cl | CH₃ | C₃H₇ |
| Cl | CH₃ | i-C₃H₇ |
| Cl | CH₃ | C₄H₉ |
| Cl | CH₃ | i-C₄H₉ |
| Cl | CH₃ | s-C₄H₉ |
| Cl | CH₃ | t-C₄H₉ |
| Cl | CH₃ | CH₂-t-C₄H₉ |
| Cl | CH₃ | CH₂—C₆H₅ |
| Cl | CH₃ | C₆H₅ |

TABLE 27

(I-c)

A = CH₃    M = S

| X | Y | R² |
|---|---|---|
| CH₃ | Cl | CH₃ |
| CH₃ | Cl | C₂H₅ |
| CH₃ | Cl | C₃H₇ |
| CH₃ | Cl | i-C₃H₇ |
| CH₃ | Cl | C₄H₉ |
| CH₃ | Cl | i-C₄H₉ |
| CH₃ | Cl | s-C₄H₉ |
| CH₃ | Cl | t-C₄H₉ |
| CH₃ | Cl | CH₂-t-C₄H₉ |
| CH₃ | Cl | CH₂—C₆H₅ |
| CH₃ | Cl | C₆H₅ |

TABLE 28

(I-c)

A = C₂H₅    M = S

| X | Y | R² |
|---|---|---|
| CH₃ | CH₃ | CH₃ |
| CH₃ | CH₃ | C₂H₅ |
| CH₃ | CH₃ | C₃H₇ |
| CH₃ | CH₃ | i-C₃H₇ |
| CH₃ | CH₃ | C₄H₉ |
| CH₃ | CH₃ | i-C₄H₉ |
| CH₃ | CH₃ | s-C₄H₉ |
| CH₃ | CH₃ | t-C₄H₉ |
| CH₃ | CH₃ | CH₂-t-C₄H₉ |
| CH₃ | CH₃ | CH₂—C₆H₅ |
| CH₃ | CH₃ | C₆H₅ |

TABLE 29

(I-c)

A = C₂H₅    M = S

| X | Y | R² |
|---|---|---|
| Br | CH₃ | CH₃ |
| Br | CH₃ | C₂H₅ |
| Br | CH₃ | C₃H₇ |
| Br | CH₃ | i-C₃H₇ |
| Br | CH₃ | C₄H₉ |
| Br | CH₃ | i-C₄H₉ |
| Br | CH₃ | s-C₄H₉ |
| Br | CH₃ | t-C₄H₉ |
| Br | CH₃ | CH₂-t-C₄H₉ |
| Br | CH₃ | CH₂—C₆H₅ |
| Br | CH₃ | C₆H₅ |

TABLE 30

(I-c)

A = C₂H₅    M = S

| X | Y | R² |
|---|---|---|
| CH₃ | Br | CH₃ |
| CH₃ | Br | C₂H₅ |
| CH₃ | Br | C₃H₇ |
| CH₃ | Br | i-C₃H₇ |
| CH₃ | Br | C₄H₉ |
| CH₃ | Br | i-C₄H₉ |
| CH₃ | Br | s-C₄H₉ |
| CH₃ | Br | t-C₄H₉ |
| CH₃ | Br | CH₂-t-C₄H₉ |
| CH₃ | Br | CH₂—C₆H₅ |
| CH₃ | Br | C₆H₅ |

TABLE 31

(I-c)

A = C₂H₅    M = S

| X | Y | R² |
|---|---|---|
| Cl | CH₃ | CH₃ |
| Cl | CH₃ | C₂H₅ |
| Cl | CH₃ | C₃H₇ |
| Cl | CH₃ | i-C₃H₇ |
| Cl | CH₃ | C₄H₉ |
| Cl | CH₃ | i-C₄H₉ |
| Cl | CH₃ | s-C₄H₉ |
| Cl | CH₃ | t-C₄H₉ |
| Cl | CH₃ | CH₂-t-C₄H₉ |
| Cl | CH₃ | CH₂—C₆H₅ |
| Cl | CH₃ | C₆H₅ |

TABLE 32

(I-c)

A = C₂H₅    M = S

| X | Y | R² |
|---|---|---|
| CH₃ | Cl | CH₃ |
| CH₃ | Cl | C₂H₅ |
| CH₃ | Cl | C₃H₇ |
| CH₃ | Cl | i-C₃H₇ |
| CH₃ | Cl | C₄H₉ |
| CH₃ | Cl | i-C₄H₉ |
| CH₃ | Cl | s-C₄H₉ |
| CH₃ | Cl | t-C₄H₉ |
| CH₃ | Cl | CH₂-t-C₄H₉ |
| CH₃ | Cl | CH₂—C₆H₅ |
| CH₃ | Cl | C₆H₅ |

Using, for example, according to process (A) ethyl cis-N-[(2,5-dimethyl)phenylacetyl]-1-amino-4-methoxycyclohexanecarboxylate as starting material, the course of the process according to the invention can be represented by the reaction scheme below:

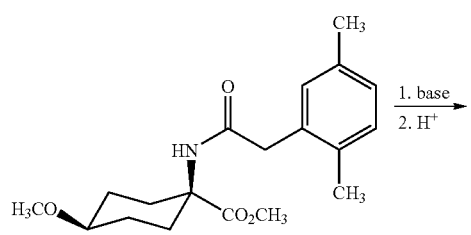

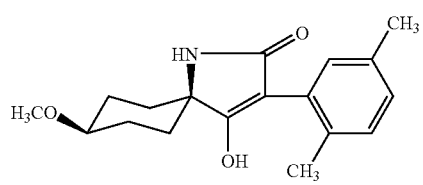

Using, for example, according to process (B-α) cis-3-[(2,5-dimethyl)phenyl]-5,5-(3-methoxy)pentamethylenepyrrolidine-2,4-dione and pivaloyl chloride as starting materials, the course of the process according to the invention can be represented by the reaction scheme below:

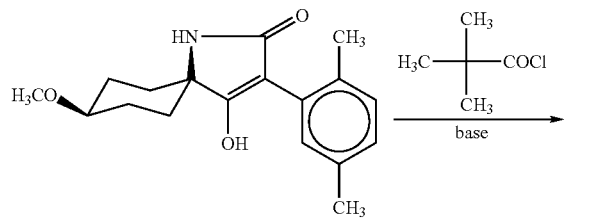

Using, for example, according to process (B-β) cis-3-[(2,5-dimethyl)phenyl]-5,5-(3-methoxy)pentamethylenepyrrolidine-2,4-dione and acetic anhydride as starting materials, the course of the process according to the invention can be represented by the reaction scheme below:

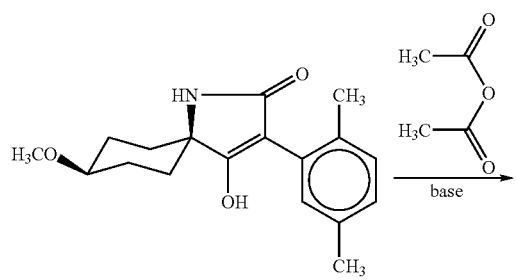

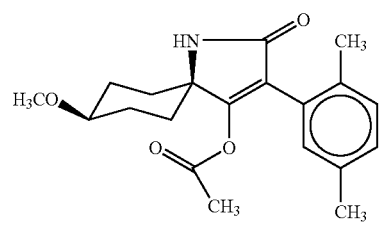

Using, for example, according to process (C) cis-3-[(2-bromo-5-methyl)phenyl]-5,5-(3-methoxy)pentamethylenepyrrolidine-2,4-dione and ethyl chloroformate as starting materials, the course of the process according to the invention can be represented by the reaction scheme below:

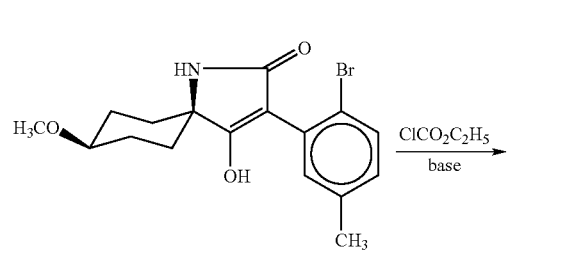

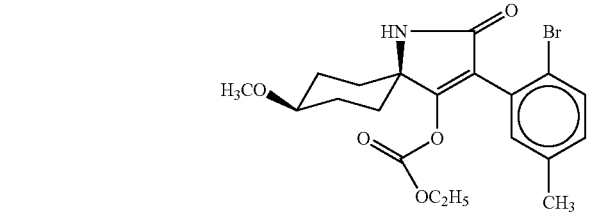

Using, for example, according to process (E) cis-3-[(2,5-dimethyl)phenyl]-5,5-(3-methoxy)pentamethylene-4-ethoxycarbonyl-Δ³-pyrrolin-2-one and aqueous bases as starting materials, the course of the process according to the invention can be represented by the reaction scheme below:

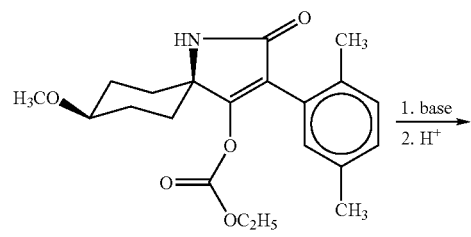

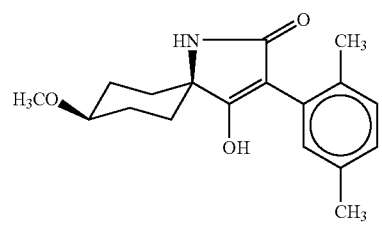

The compounds of the formula (II) required as starting materials for the process (A) according to the invention

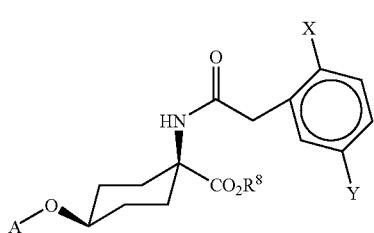
(II)

in which

A, X, Y and $R^8$ are as defined above are novel.

The acylamino acid esters of the formula (II) are obtained, for example, when cis-amino acid derivatives of the formula (VI)

(VI)

in which

A, B and $R^8$ are as defined above are acylated with substituted phenylacetic acid halides of the formula (VII)

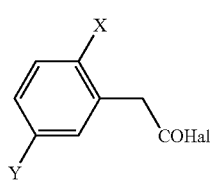
(VII)

in which

X and Y are as defined above and

Hal represents chlorine or bromine (Chem. Reviews 52, 237-416 (1953); Bhattacharya, Indian J. Chem. 6, 341-5, 1968)

or when acylamino acids of the formula (VIII)

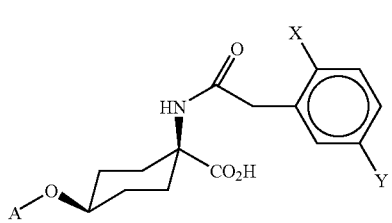
(VIII)

in which

A, X and Y are as defined above are esterified (Chem. Ind. (London) 1568 (1968)).

The compounds of the formula (VIII)

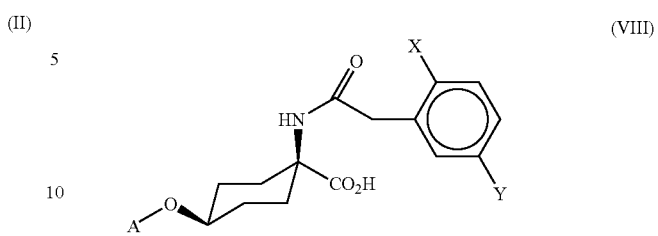
(VIII)

in which

A, X and Y are as defined above are novel.

The compounds of the formula (VIII) are obtained when cis-amino acids of the formula (IX)

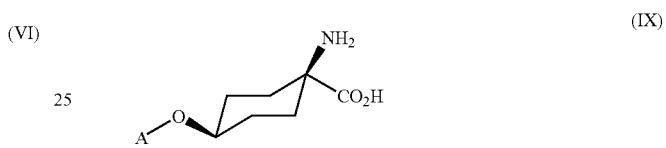
(IX)

in which

A is as defined above are acylated with substituted phenylacetic acid halides of the formula (VII)

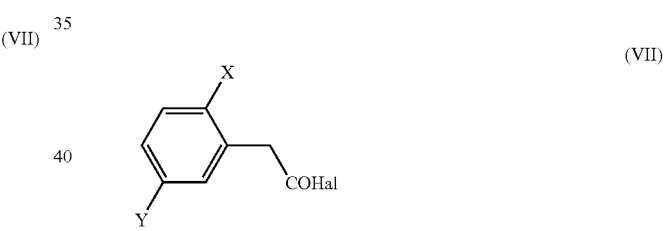
(VII)

in which

X and Y are as defined above and

Hal represents chlorine or bromine according to Schotten-Baumann (Organikum, VEB Deutscher Verlag der Wissen-schaften, Berlin 1977, p. 505).

The compounds of the formula (VII) are known (WO 98/05638, WO 01/74770) or can be prepared by the processes described in these references.

The compounds of the formulae (VI) and (IX) are known (WO 02/02532) or can be prepared by the processes described in this reference.

The acid halides of the formula (III), carboxylic anhydrides of the formula (IV) and chloroformic esters and chloroformic thioesters of the formula (V) furthermore required as starting materials for carrying out the processes (B) and (C) according to the invention are generally known compounds of organic or inorganic chemistry.

The process (A) is characterized in that compounds of the formula (II) in which A, X, Y and $R^8$ are as defined above are subjected to an intramolecular condensation in the presence of a diluent and in the presence of a base.

Suitable diluents for the process (A) according to the invention are all organic solvents which are inert to the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethyl formamide and N-methylpyrrolidone, and also alcohols, such as methanol, ethanol, propanol, isopropanol, butanol, isobutanol and tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutyl-ammonium bromide, Adogen 464 (=methyltrialkyl($C_8$-$C_{10}$)ammonium chloride) or TDA 1 (=tris(methoxyethoxyethyl)amine). It is furthermore possible to use alkali metals such as sodium or potassium. Also suitable are alkali metal and alkaline earth metal amides and hydrides, such as sodium amide, sodium hydride and calcium hydride, and furthermore also alkali metal alkoxides, such as sodium methoxide, sodium ethoxide and potassium tert-butoxide.

When carrying out the process (A) according to the invention, the reaction temperature can be varied within a relatively wide range. In general, the process is carried out at temperatures between 0° C. and 250° C., preferably between 50° C. and 150° C.

The process (A) according to the invention is generally carried out under atmospheric pressure.

When carrying out the process (A) according to the invention, the reaction component of the formula (II) and the deprotonating base are generally employed in equimolar to about double-equimolar amounts. However, it is also possible to use a relatively large excess (up to 3 mol) of one component or the other.

The process (Bα) is characterized in that compounds of the formula (I-a) are reacted with carbonyl halides of the formula (III), if appropriate in the presence of a diluent and if appropriate in the presence of an acid binder.

Suitable diluents for the process (B-α) according to the invention are all solvents which are inert to the acid halides. Preference is given to using hydrocarbons, such as benzine, benzene, toluene, xylene and tetralene, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethylformamide, dimethyl sulphoxide and sulpholane. The hydrolytic stability of the acid halide permitting, the reaction can also be carried out in the presence of water.

Suitable acid binders for the reaction according to the process (Bα) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

The reaction temperature in the process (Bα) according to the invention can be varied within a relatively wide range. In general, the process is carried out at temperatures between −20° C. and +150° C., preferably between 0° C. and 100° C.

When carrying out the process (Bα) according to the invention, the starting materials of the formula (I-a) and the carbonyl halide of the formula (III) are generally each employed in approximately equivalent amounts. However, it is also possible to use a relatively large excess (up to 5 mol) of the carbonyl halide. Work-up is carried out by customary methods.

The process (Bβ) is characterized in that compounds of the formula (I-a) are reacted with carboxylic anhydrides of the formula (IV), if appropriate in the presence of a diluent and if appropriate in the presence of an acid binder.

Suitable diluents for the process (Bβ) according to the invention are, preferably, those diluents which are also preferred when using acid halides. Moreover, excess carboxylic anhydride may simultaneously act as diluent.

Preferred acid binders for the process (Bβ), which are added, if appropriate, are those acid binders which are also preferred when using acid halides.

The reaction temperature for the process (Bβ) according to the invention can be varied within a relatively wide range. In general, the process is carried out at temperatures between −20° C. and +150° C., preferably between 0° C. and 100° C.

When carrying out the process (Bβ) according to the invention, the starting materials of the formula (I-a) and the carboxylic anhydride of the formula (IV) are generally each employed in approximately equivalent amounts. However, it is also possible to use a relatively large excess (up to 5 mol) of the carboxylic anhydride. Work-up is carried out by customary methods.

In general, diluent and excess carboxylic anhydride and the carboxylic acid formed are removed by distillation or by washing with an organic solvent or with water.

The process (C) is characterized in that compounds of the formula (I-a) are reacted with chloroformic esters or chloroformic thiol esters of the formula (V), if appropriate in the presence of a diluent and if appropriate in the presence of an acid binder.

Suitable acid binders for the process (C) according to the invention are all customary acid acceptors. Preference is given to using tertiary amines, such as triethylamine, pyridine, DABCO, DBU, DBA, Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable diluents for the process (C) according to the invention are all solvents which are inert to the chloroformic esters or chloroformic thiol esters. Preference is given to using hydrocarbons, such as benzine, benzene, toluene, xylene and tetralene, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, moreover nitrites, such as acetonitrile, and also strongly polar solvents, such as dimethylformamide, dimethyl sulphoxide and sulpholane.

When carrying out the process (C) according to the invention, the reaction temperature can be varied within a relatively wide range. The reaction temperature is generally between −20° C. and +100° C., preferably between 0° C. and 70° C.

The process (C) according to the invention is generally carried out under atmospheric pressure.

When carrying out the process (C) according to the invention, the starting materials of the formula (I-a) and the appropriate chloroformic ester or chloroformic thioester of the formula (V) are generally each employed in approximately equivalent amounts. However, it is also possible to use a relatively large excess (up to 2 mol) of one component or the other. Work-up is carried out by customary methods. In general, precipitated salts are removed and the reaction mixture that remains is concentrated by removing the diluent under reduced pressure.

The process (E) according to the invention is characterized in that compounds of the formulae (I-b) or, if appropriate, (I-c) are hydrolysed in the presence of a solvent and in the presence of a base in aqueous medium and then acidified with acids.

In the preparation process (E), one mole of the starting materials of the formula (I-b) is reacted with about 1 to 10 mol, preferably 1 to 3 mol, of base, at from 0 to 150° C., preferably from 20 to 80° C.

Suitable diluents, which are added, if appropriate, are all organic solvents which are readily miscible with water, such as alcohols, ethers, amides, sulphones or sulphoxides.

Preference is given to using methanol, ethanol, propanol, isopropanol, butanol, isobutanol, tetrahydrofuran, dioxane, dimethylformamide, dimethylacetamide, N-methylpyrrolidone, sulpholane or dimethyl sulphoxide.

Inorganic acids and organic acids which are preferably used for acidification are hydrochloric acid, sulphuric acid, phosphoric acid or nitric acid and formic acid, acetic acid or sulphonic acids, respectively.

The process (D) according to the invention is characterized in that cis/trans isomer mixtures of the formulae (I-b') or (I-c') are separated by chromatographic methods, preferably by column chromatography on silica gel.

In the preparation process (D), about 10 g to 200 g, preferably from 50 to 100 g, of silica gel are employed per gram of starting material.

The mobile phases used are solvent mixtures of varying polarity. Preference is given to using solvent mixtures of halogenated hydrocarbons combined with ketones, esters or alcohols.

The process (D) according to the invention is generally carried out under atmospheric pressure. It is also possible to operate under elevated pressures such as pressures present, for example, when a separation is carried out using MPLC or HPLC units.

The active compounds are suitable for controlling animal pests, in particular insects, arachnids and nematodes, which are encountered in agriculture, in forestry, in the protection of stored products and of materials, and in the hygiene sector, and have good plant tolerance and favourable toxicity to warm-blooded animals. They may be preferably employed as plant protection agents. They are active against normally sensitive and resistant species and against all or some stages of development. The abovementioned pests include:

From the order of the Isopoda, for example, *Oniscus asellus, Annadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, *Reticulitennes* spp.

From the order of the Phthiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis, Thrips tabaci, Thrips palmi* and *Frankliniella accidentalis.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Farmia* spp., *Calliphora erythrocephala, Lucilia* spp.,

*Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus, Latrodectus mactans, Acarus siro, Argas* spp., *Omithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

The phytoparasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

If appropriate, the compounds according to the invention can, at certain concentrations or application rates, also be used as herbicides or microbicides, for example as fungicides, antimycotics and bactericides. If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on and, in the case of propagation material, in particular in the case of seeds, also by applying one or more coats.

The active compounds can be converted into the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds with extenders, that is, liquid solvents, and/or solid carriers, optionally with the use of surfactants, that is emulsifiers and/or dispersants, and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

Suitable solid carriers include:

for example ammonium salts and ground natural minerals such as kaolins, clays, talc, chalk, quartz, attapulgite, montmorillonite or diatomaceous earth, and ground synthetic minerals, such as highly disperse silica, alumina and silicates; suitable solid carriers for granules include: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers include: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants include: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention can be used as such or in their formulations, also as a mixture with known fungicides, bactericides, acaricides, nematicides, or insecticides, in order, in this way, for example, to broaden the spectrum of activity or to prevent the development of resistance. In many cases, synergistic effects are obtained, i.e. the activity of the mixture exceeds the activity of the individual components.

Suitable co-components are, for example, the following compounds:

Fungicides:

aldimorph, ampropylfos, ampropylfos-potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dim ethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulphamide, flutolanil, flutriafol, folpet, fosetyl-aluminium, fosetyl-sodium, fthalide, fuberidazole, furalaxyl, furamnetpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulphocarb, methfuroxam, metiram, metomeclam, metsulphovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, picoxystrobin, pimaricin, piperalin, polyoxin, polyoxorim, probenazole, prochloraz, procymidone, propamocarb, propanosine-sodium, propiconazole, propineb, pyraclostrobin, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, trifloxystrobin, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4-(trifluoromethyl)phenyl]methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxyphenylacetamide, 1-isopropyl {2-methyl-1-[[[1-(4-methylphenyl)ethyl]amino]carbonyl]propyl}carbamate, 1-(2,4-dichlorophenyl)-2-(1H-1,2,4-triazol-1-yl)ethanone-O-(phenylmethyl)oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)sulphonyl]-4-methyl-benzene, 1-[[2-(2,4-dichlorophenyl)-1,3-dioxolan-2-yl]methyl]-1H-imidazole, 1-[[2-(4-chlorophenyl)-3-phenyloxiranyl]methyl]-1H-1,2,4-triazole, 1-[1-[2-[(2,4-dichlorophenyl)methoxy]phenyl]ethenyl]-1H-imidazole, 1-methyl-5-nonyl-2-(phenylmethyl)-3-pyrrolidinole, 2',6'-dibromo-2-methyl-4'-trifluoromethoxy-4'-trifluoromethyl-1,3-thiazole-5-carboxanilide, 2,2-dichloro-N-[1-(4-chlorophenyl)ethyl]-1-ethyl-3-methyl-cyclopropanecarboxamide, 2,6-dichloro-5-(methylthio)-4-pyrimidinylthiocyanate, 2,6-dichloro-N-(4-trifluoromethylbenzyl)benzamide, 2,6-dichloro-N-[[4-(trifluoromethyl)phenyl]methyl]benzamide, 2-(2,3,3-triiodo-2-propenyl)-2H-tetrazole, 2-[(1-methylethyl)sulphonyl]-5-(trichloromethyl)-1,3,4-thiadiazole, 2-[[6-deoxy-4-O-(4-O-methyl-β-D-glycopyranosyl)-α-D-glucopyranosyl]amino]-4-methoxy-1H-pyrrolo[2,3-d]pyrimidine-5-carbonitrile, 2-aminobutane, 2-bromo-2-(bromomethyl)pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)acetamide, 2-phenylphenol (OPP), 3,4-dichloro-1[4-(difluoromethoxy)phenyl]-1H-pyrrole-2,5-dione, 3,5-dichloro-N-[cyano[(1-methyl-2-propynyl)oxy]methyl]benzamide, 3-(1,1-dimethylpropyl)-1-oxo-1H-indene-2-carbonitrile, 3-[2-(4-chlorophenyl)-5-ethoxy-3-isoxazolidinyl]pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulphate, 9H-xanthene-2-[(phenylamino)carbonyl]-9-carboxylic hydrazide, bis-(1-methylethyl)-3-methyl-4-[(3-methylbenzoyl)oxy]-2,5-thiophenedicarboxylate, cis-1-(4-chlorophenyl)-2-(1H-1,2,4-triazol-1-yl)cycloheptanol, cis-4-[3-[4-(1,1-dimethylpropyl)-phenyl-2-methylpropyl]-2,6-dimethylmorpholine hydrochloride, ethyl[(4-chlorophenyl)azo]cyanoacetate, potassium bicarbonate, methanetetrathiol-sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methylcyclohexanecarboxamide,
N-(2,6-dimethylphenyl)-2-methoxy-N-(tetrahydro-2-oxo-3-furanyl)acetamide,
N-(2,6-dimethylphenyl)-2-methoxy-N-(tetrahydro-2-oxo-3-thienyl)acetamide,
N-(2-chloro-4-nitrophenyl)-4-methyl-3-nitrobenzenesulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)acetamide,
N-(6-methoxy)-3-pyridinyl)cyclopropanecarboxamiide,
N-[2,2,2-trichloro-1-[(chloroacetyl)amino]ethyl]benzamnide,
N-[3-chloro-4,5-bis(2-propinyloxy)phenyl]-N'-methoxymethanimidamide,
N-formyl-N-hydroxy-DL-alanine sodium salt,
O,O-diethyl [2-(dipropylamino)-2-oxoethyl]ethylphosphoramidothioate,
O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran]-3'-one,
4-[3,4-(dimethoxyphenyl)-3-(4-fluorophenyl)-acryloyl] morpholine.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/acaricides/nematicides:

abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis,* baculoviruses, *Beauveria bassiana, Beauveria tenella,* benidiocarb, benfuracarb, bensultap, benzoximate, betacyfluthrin, bifenazate, bifenthrin, bioethanomethrin, biopermethrin, bistrifluron, BPMC, bromophos A, bufencarb, buprofezin, butathiofos, butocarboxim, butylpyridaben, cadusafos, carbaryl, carbofuran, carbophenothion, carbosulphan, cartap, chloethocarb, chlorethoxyfos, chlorfenapyr, chlorfenvinphos, chlorfluazuron, chlormephos, chlorpyrifos, chlorpyrifos M, chlovaporthrin, chromafenozide, cisresmethrin, cispermethrin, clocythrin, cloethocarb, clofentezine, clothianidine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, dicofol, diflubenzuron, dimethoate, dimnethylvinphos, diofenolan, disulphoton, docusat-sodium, dofenapyn, eflusilanate, emamectin, empenthrin, endosulphan, *Entomopfthora* spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flumethrin, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, indoxacarb, isazofos, isofenphos, isoxathion, ivermectin, nuclear polyhedrosis viruses, lambda-cyhalothrin, lufenuron, malathion, mecarbam, metaldehyde, methamidophos, *Metharhizium anisopliae, Metharhizium flavoviride,* methidathion, methiocarb, methoprene, methomyl, methoxyfenozide, metolcarb, metoxadiazone, mevinphos, milbemectin, milbemycin, monocrotophos, naled, nitenpyram, nithiazine, novaluron, omethoate, oxamyl, oxydemethon M,

*Paecilomyces fumosoroseus,* parathion A, parathion M, permethrin, phenthoate, phorate, phosalone, phosmet, phosphamidon, phoxim, pirimicarb, pirimiphos A, pirimiphos M, profenofos, promecarb, propargite, propoxur, prothiofos, prothoate, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, spirodiclofen, sulphotep, sulprofos, tau-fluvalinate, tebufenozide, tebufenpyrad, tebupirimiphos, teflubenzuron, tefluthrin, temephos, temivinphos, terbufos, tetrachlorvinphos, tetradifon, theta-cypermethrin, thiacloprid, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii,*

YI 5302, zeta-cypermethrin, zolaprofos, (1R-cis)-[5-(phenylmethyl)-3-furanyl]methyl 3-[(dihydro-2-oxo-3(2H)-faranylidene)methyl]-2,2-dimethylcyclopropanecarboxylate,
(3-phenoxyphenyl)-methyl-2,2,3,3-tetramethylcyclopropanecarboxylate,
1-[(2-chloro-5-thiazolyl)methyl]tetrahydro-3,5-dimethyl-N-nitro-1,3,5-triazine-2(1H)-imine,
2-(2-chloro-6-fluorophenyl)-4-[4-(1,1-dimethylethyl)phenyl]-4,5-dihydrooxazole,
2-(acetyloxy)-3-dodecyl-1,4-naphthalenedione,
2-chloro-N-[[[4-(1-phenylethoxy)phenyl]amino]carbonyl] benzamide,
2-chloro-N-[[[4-(2,2-dichloro-1,1-difluoroethoxy)phenyl] amino]carbonyl]benzamide,
3-methylphenyl propylcarbamate,
4-[4-(4-ethoxyphenyl)-4-methylpentyl]-1-fluoro-2-phenoxybenzene, 4-chloro-2-(1,1-dimethylethyl)-5-[[2-(2,6-dimethyl-4-phenoxyphenoxy)ethyl]thio]-3(2H)-pyridazinone,
4-chloro-2-(2-chloro-2-methylpropyl)-5-[(6-iodo-3-pyridinyl)methoxy]-3(2H)-pyridazinone,
4-chloro-5-[(6-chloro-3-pyridinyl)methoxy]-2-(3,4-dichlorophenyl)-3(2H)-pyridazinone,
*Bacillus thuringiensis* strain EG-2348,
2-benzoyl-1-(1,1-dimethylethyl)-hydrazinobenzoic acid,
2,2-dimethyl-3-(2,4-dichlorophenyl)-2-oxo-1-oxaspiro[4.5]dec-3-en-4-yl butanoate,
[3-[(6-chloro-3-pyridinyl)methyl]-2-thiazolidinylidene]cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]carbamate, N-(3,4,4-trifluoro-1-oxo-3-butenyl)glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N"-nitroguanidine, N-methyl-N'-(1-methyl-2-propenyl)-1,2-hydrazinedicarbothioamide, N-methyl-N'-2-propenyl-1,2-hydrazinedicarbothioamide, O,O-diethyl [2-(dipropylamino)-2-oxoethyl]ethylphosphoramidothioate, N-cyanomethyl-4-trifluoromethylnicotinamide 3,5-dichloro-1-(3,3-dichloro-2-propenyloxy)-4-[3-(5-trifluoromethylpyridin-2-yloxy)propoxy]benzene.

It is also possible to admix other known active compounds, such as herbicides, fertilizers and growth regulators.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by genetic engineering. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful traits to these plants. Examples of such traits are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defense of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the increased defense of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosates or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones)

and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plants will be developed and/or marketed in the future.

The plants listed can be treated according to the invention in a particularly advantageous manner with the compounds of the formula (I) and/or the active compound mixtures according to the invention. The preferred ranges stated above for the active compounds and/or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Wemeckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Hiaematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattella germanica* and *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) und Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention have a strong insecticidal action against insects which destroy industrial materials.

The following insects may be mentioned as examples and as preferred—but without a limitation:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Hymenopterons, such as

*Sirex juvencus, Urocerus gigas, Urocerus gigas taignus, Urocerus augur.*

Termites, such as

*Kaloterrnes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccarina.*

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agent according to the invention or mixtures comprising it are to be understood as meaning, for example:

building timber, wooden beams, railway sleepers, bridge components, boat jetties, wooden vehicles, boxes, pallets, containers, telegraph poles, wood paneling, wooden windows and doors, plywood, chipboard, joinery or wooden products which are used quite generally in house-building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, provided that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or a drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the abovementioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyfenozide and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The compounds according to the invention can at the same time be employed for protecting objects which come into contact with saltwater or brackish water, such as hulls, screens, nets, buildings, moorings and signalling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operational costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulphides, tri-n-butyltin laurate, tri-n-butyltin chloride, copper (I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylenebisthio-carbamate, zinc dimethyldithiocarbamate, zinc ethylenebisthiocarbamate, zinc salts and copper salts of 2-pyridinethiol 1-oxide, bisdimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:

algicides such as 2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;

fungicides such as benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;

molluscicides such as fentin acetate, metaldehyde, methiocarb, niclosamid, thiodicarb and trimethacarb; or conventional antifouling active compounds such as 4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/-styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, Avicularriidae, Araneidae.

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Phthirus pubis.*

From the order of the Heteroptera, for example, *Cimex hemipterus, Cimex lectularius, Rhodinus prolixus, Triatoma infestans.*

In the field of household insecticides, they are used alone or in combination with other suitable active compounds, such as phosphoric acid esters, carbamates, pyrethroids, growth regulators or active compounds from other known classes of insecticides.

They are used as aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The preparation and use of the active compounds according to the invention are illustrated by the examples below.

PREPARATION EXAMPLES

Example (I-a-1)

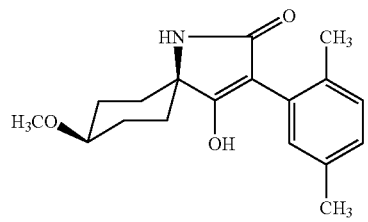

Process A:

At room temperature, a solution of 53.3 g (0.16 mol) of the compound according to Preparation Example (II-1) (99% pure, cis/trans 97:3) in 160 ml of dimethylformamide (DMF) is added dropwise to a solution of 30% strength methanolic NaOMe solution (72 g, 0.4 mol) in 240 ml of DMF (with the methanol being completely removed beforehand by distillation).

The reaction mixture is heated to 60° C. and stirred at 60° C. for 4 h.

The methanol formed during the reaction is distilled off under slight vacuum. At 50-60° C., a mixture of 32% strength hydrochloric acid (96 ml) and 960 ml of water is then added dropwise. The solution is stirred at room temperature for 1 h and the solid is filtered off with suction, washed 2× with in each case 200 ml of water and dried.

Yield: 44.16 g (91.6% of theory), m.p. 224-228° C.

Example (I-a-2)

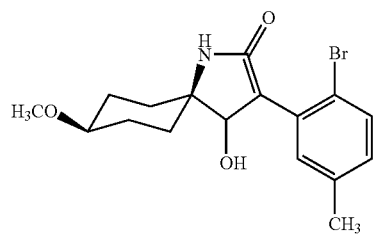

Process E:

1.75 g of the compound of Example (I-c-2) are initially charged in 5 ml of ethanol, and 0.5 g of NaOH in 4 ml of water is added dropwise at room temperature. The mixture is stirred at 40-50° C. and the reaction is monitored by thin-layer chromatography.

When the reaction has ended, the ethanol is distilled off and the residue is made up with water to a volume of 10 ml. At 0-10° C., the mixture is acidified with concentrated hydrochloric acid and the precipitate is filtered off with suction and dried.

Yield: 1.35 g (92% of theory), m.p. 274° C.

Analogously to Example (I-a-2), Example (I-a-1) of melting point 226° C. is obtained according to Process E.

Example (I-c-1)

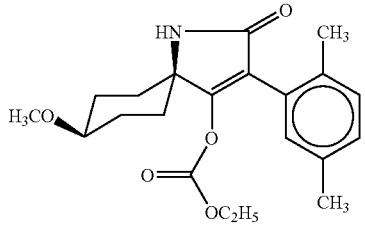

Process C 3.02 g (10 mmol) of the compound of Example (I-a-1) and 1.21 g (12 mmol) of triethylamine are initially charged in 20 ml of chlorobenzene. At 60-65° C., a solution of 1.14 g (10.5 mmol) of ethyl chloroformate in 8 ml of chlorobenzene is then added dropwise. The mixture is stirred at 60-65° C. for 4 h. At room temperature, the reaction solution is diluted with 20 ml of chlorobenzene and extracted with 20 ml of water, 20 ml of 5% strength aqueous sodium hydroxide solution and finally with 10 ml of saturated aqueous NaCl solution, the organic phase is dried and the solvent is distilled off. This gives 3.88 g of crude product, 1.523 g of which were recrystallized from 15 ml of methylcyclohexane. This gave 1.437 g of product; accordingly, the calculated yield for the total amount of I-c-1 is 3.72 g. Based on a purity of 99.6%, the yield is 3.68 g ($\geq$98.6% of theory), m.p. 142-143° C.

Example (II-1)

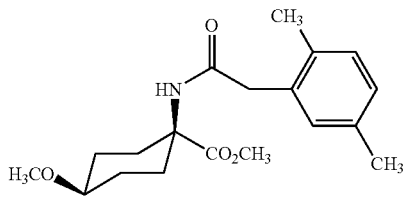

107 g (0.43 mol) of methyl cis-4-methoxycyclohexane-1-aminocarboxylate hydrochloride (WO 02/02532, Ex. 15) and 221 g (1.6 mol) of potassium carbonate are initially charged in 370 ml of acetonitrile.

At 5-10° C., a solution of 75.1 g (0.4 mol) of 2,5-dimethylphenylacetyl chloride in 140 ml of acetonitrile is added dropwise.

The mixture is then stirred at room temperature for 3 h. Subsequently, the reaction mixture is added to 2 l of ice-water. The mixture is stirred for about 1 h and the precipitate is filtered off with suction, washed 3 times with in each case 150 ml of water and then dried.

Yield: 131 g (98.2% of theory), m.p. 101-102° C.

Example (I-c-2)

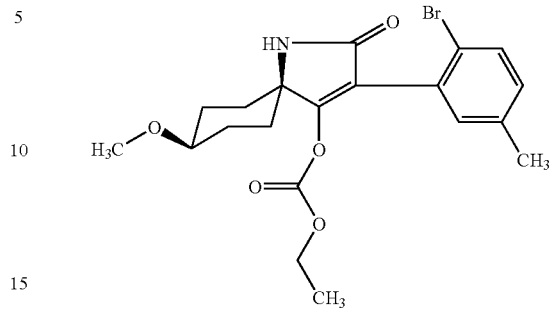

Process D 9.4 ml (67 mmol) of triethylamine are added to 24.68 g of the compound of Example (I-1-a-28) (WO 98/05638) in 560 ml of anhydrous dichloromethane, and 6.7 ml (67 mmol) of ethyl chloroformate in 56 ml of anhydrous $CH_2Cl_2$ are added dropwise at 0-10° C.

The mixture is stirred at room temperature and the reaction is monitored by thin-layer chromatography.

After the reaction has ended, the solvent is distilled off and the residue is washed twice with 500 ml of 0.5 N NaOH solution. The organic phase is dried, the solvent is distilled off and the residue is purified by column chromatography (silica gel, dichloromethane/ethyl acetate 3:1)

Yield: 9.82 g (33% of theory), m.p. 159° C.

The cis isomer (I-c-2) (9.82 g) obtained according to Process D is again purified by column chromatography on silica gel using dichloromethane/acetone 5:1.

Yield: 4.24 g (14% of theory), m.p. 164° C.

Analogously to Example (I-c-2), silica gel chromatography using $CH_2Cl_2$/acetone 5:1 gives Example (I-c-1) of melting point 144° C.

Example (I-c-4)

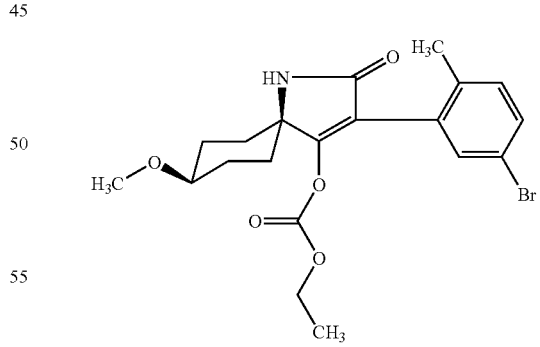

Process D 0.8 g of a cis/trans isomer mixture (about 81:18) of the compound of Example I-1-c-32 from WO 98/05638 was chromatographed on silica gel using the mobile phase methylene chloride/ethyl acetate 2:1.

Yield: 0.51 g, m.p. 160° C.

Purity by HPLC (area per cent)>99%.

Analogously to Examples (I-c-1) and (I-c-2) and in accordance with the general statements concerning the preparation and isolation, the following compounds of the formula (I-c) are obtained

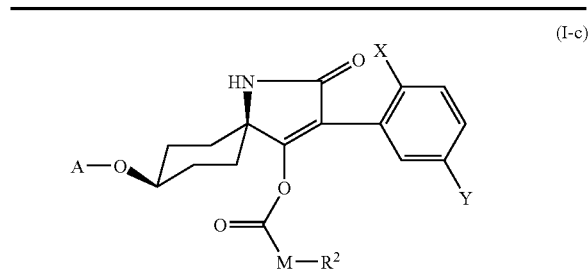
(I-c)

| Ex. No. | X | Y | A | M | R² | m.p.° C. |
|---|---|---|---|---|---|---|
| I-c-3 | Br | CH₃ | CH₃ | O | C₆H₅—CH₂— | 171 |

Analogously to Examples (I-c-1) and (I-c-2) and in accordance with the general statements concerning the preparation and isolation, the following compounds of the formula (I-b) are obtained

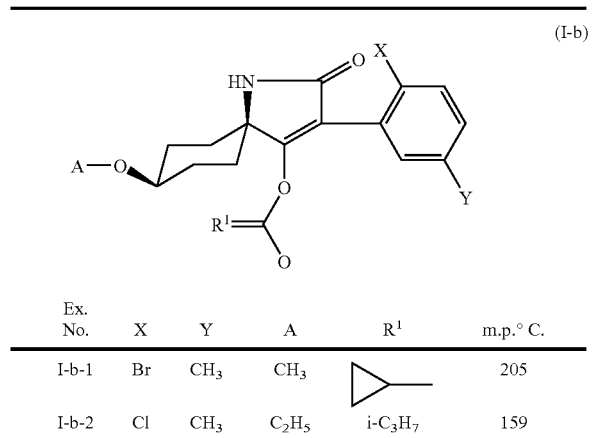
(I-b)

| Ex. No. | X | Y | A | R¹ | m.p.° C. |
|---|---|---|---|---|---|
| I-b-1 | Br | CH₃ | CH₃ | △ | 205 |
| I-b-2 | Cl | CH₃ | C₂H₅ | i-C₃H₇ | 159 |

Example A

*Aphis gossypii* Test

Solvent: 7 parts by weight of dimethylformamide

Emulsifier: 2 parts by weight of alkylaryl polyglycol ether

To produce a suitable preparation of active compound, 1 part by weight of active compound is mixed with the stated amounts of solvent and emulsifier, and the concentrate is diluted with emulsifier-containing water to the desired concentration.

Cotton leaves (*Gossypium hirsutum*) which are heavily infested by the cotton aphid (*Aphis gossypii*) are treated by being dipped into the preparation of active compound of the desired concentration.

After the desired period of time, the kill in % is determined. 100% means that all aphids have been killed; 0% means that none of the aphids have been killed.

In this test, for example, the following compound of the Preparation Examples shows an efficacy which is superior to the prior art:

TABLE A

| | plant-damaging insects *Aphis gossipii* Test | |
|---|---|---|
| Active compounds | Concentration of active compound in ppm | Kill rate in % after 6ᵈ |
| Example I-1-c-4 known from WO98/05638 | 40 | 70 |
| Example I-c-1 according to the invention | 20 | 90 |

Example B

*Heliothis virescens* Test

Solvent: 7 parts by weight of dimethylformamide

Emulsifier: 2 parts by weight of alkylaryl polyglycol ether

To produce a suitable preparation of active compound, 1 part by weight of active compound is mixed with the stated amounts of solvent and emulsifier, and the concentrate is diluted with emulsifier-containing water to the desired concentration.

Soybean shoots (*Glycine max*) are treated by being dipped into the preparation of active compound of the desired concentration and are populated with *Heliothis virescens* caterpillars while the leaves are still moist.

After the desired period of time, the kill in % is determined. 100% means that all caterpillars have been killed; 0% means that none of the caterpillars have been killed.

In this test, for example, the following compound of the Preparation Examples shows an efficacy which is superior to the prior art:

TABLE B

| | plant-damaging insects *Heliothis virescens* Test | |
|---|---|---|
| Active compounds | Concentration of active compound in ppm | Kill rate in % after 6ᵈ |
| Example I-1-c-22 known from WO98/05638 | 500 | 65 |
| Example I-c-2 according to the invention | 500 | 100 |

Example C

*Phaedon* Larvae Test

Solvent: 7 parts by weight of dimethylformamide

Emulsifier: 2 parts by weight of alkylaryl polyglycol ether

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

In this test, for example, the following compound of the Preparation Examples shows an efficacy which is superior to the prior art:

TABLE C plant-damaging insects
*Phaedon* Larvae Test

| Active compounds | Concentration of active compound in ppm | Kill rate in % after $7^d$ |
|---|---|---|
| Example I-1-c-4 known from WO98/05638 | 100 | 90 |
| | 10 | 0 |
| Example I-c-1 according to the invention | 100 | 100 |
| | 20 | 80 |

Example D

*Plutella* Test

Resistant Strain

Solvent: 7 parts by weight of dimethylformamide

Emulsifier: 2 parts by weight of alkylaryl polyglycol ether

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the diamondback moth (*Plutella xylostella*/resistant strain) while the leaves are still moist.

After the desired period of time, the kill in % is determined. 100% means that all caterpillars have been killed; 0% means that none of the caterpillars have been killed.

In this test, for example, the following compound of the Preparation Examples shows an efficacy which is superior to the prior art:

TABLE D plant-damaging insects
Plutella Test (resistant strain)

| Active compounds | Concentration of active compound in ppm | Kill rate in % after $6^d$ |
|---|---|---|
| Example I-1-c-22 known from WO98/05638 | 4 | 75 |
| Example I-c-2 according to the invention | 4 | 100 |

Example E

*Tetranychus* Test

OP-Resistant/Dip Treatment

Solvent: 7 parts by weight of dimethylformamide

Emulsifier: 2 parts by weight of alkylarylpolyglycol ether

To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are heavily infested by all stages of the greenhouse red spider mite (*Tetranychus urticae*) are dipped into a preparation of active compound of the desired concentration.

After the desired period of time, the activity in % is determined. 100% means that all spider mites have been killed; 0% means that none of the spider mites have been killed.

In this test, for example, the following compound of the Preparation Examples shows an efficacy which is superior to the prior art:

TABLE E plant-damaging mites
*Tetranychus* Test (OP-resistant/dip treatment)

| Active compounds | Concentration of active compound in ppm | Kill rate in % after $7^d$ |
|---|---|---|
| Example I-1-a-28 known from WO98/05638 | 1 | 0 |
| Example I-a-2 according to the invention | 0.8 | 80 |

Example F

*Myzus* Test

Solvent: 7 parts by weight of dimethylformamide

Emulsifier: 2 parts by weight of alkylaryl polyglycol ether

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) which are heavily infested by the peach aphid (*Myzus persicae*) are treated by being dipped into the preparation of active compound of the desired concentration.

After the desired period of time, the kill in % is determined. 100% means that all aphids have been killed; 0% means that none of the aphids have been killed.

In this test, for example, the following compound of the Preparation Examples shows an efficacy which is superior to the prior art:

TABLE F plant-damaging insects
*Myzus* Test

| Active compounds | Concentration of active compound in ppm | Kill rate in % after $6^d$ |
|---|---|---|
| Example I-1-c-32 known from WO 98/05638 | 10 | 20 |
| Example I-c-4 according to the invention | 4 | 50 |
| Example I-1-b-47 known from WO 98/05638 | 100 | 60 |
| Example I-b-1 according to the invention | 100 | 80 |

Example G

Phaedon Larvae Test

Solvent: 7 parts by weight of dimethylformamide

Emulsifier: 2 parts by weight of alkylaryl polyglycol ether

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

In this test, for example, the following compound of the Preparation Examples shows an efficacy which is superior to the prior art:

TABLE G plant-damaging insects
*Phaedon* Larvae Test

| Active compounds | Concentration of active compound in ppm | Kill rate in % after $7^d$ |
|---|---|---|
| Example I-1-a-4 known from WO 98/05638 | 100 | 0 |
| Example I-a-1 according to the invention | 100 | 100 |
| Example I-1-c-32 known from WO 98/05638 | 100 | 0 |
| Example I-c-4 according to the invention | 100 | 25 |

Example H

Spodoptera frugiperda Test

Solvent: 7 parts by weight of dimethylformamide

Emulsifier: 2 parts by weight of alkylaryl polyglycol ether

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the armyworm (*Spodoptera frugiperda*) while the leaves are still moist.

After the desired period of time, the kill in % is determined. 100% means that all caterpillars have been killed; 0% means that none of the caterpillars have been killed.

In this test, for example, the following compound of the Preparation Examples shows an efficacy which is superior to the prior art:

TABLE H plant-damaging insects
*Spodoptera frugiperda* Test

| Active compounds | Concentration of active compound in ppm | Kill rate in % after $7^d$ |
|---|---|---|
| Example I-1-a-4 known from WO 98/05638 | 100 | 35 |
| Example I-a-1 according to the invention | 100 | 50 |
| Example I-1-c-32 known from WO 98/05638 | 100 | 0 |
| Example I-c-4 according to the invention | 100 | 20 |
| Example I-1-c-39 known from WO 98/05638 | 1000 | 80 |
| Example I-c-3 according to the invention | 500 | 100 |
| Example I-1-b-47 known from WO 98/05638 | 100 | 0 |
| Example I-b-1 according to the invention | 100 | 60 |

Example I

Tetranychus Test

OP-Resistant/Spray Treatment

Solvents: 78 parts by weight of acetone
1.5 parts by weight of dimethylformamide Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Discs of bean leaves (*Phaseolus vulgaris*) which are heavily infested by all stages of the greenhouse red spider mite (*Tetranychus urticae*) are sprayed with a preparation of active compound of the desired concentration.

After the desired period of time, the activity in % is determined. 100% means that all spider mites have been killed; 0% means that none of the spider mites have been killed.

In this test, for example, the following compound of the Preparation Examples shows an efficacy which is superior to the prior art:

TABLE I plant-damaging mites
Tetranychus Test
(OP-resistant/spray treatment)

| Active compounds | Concentration of active compound in ppm | Kill rate in % after $4^d$ |
|---|---|---|
| 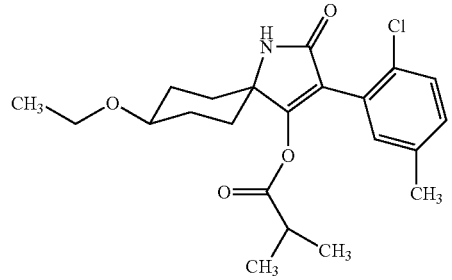 | 100 | 70 |
| Example I-b-2 according to the invention | 100 | 100 |

Example J

Tetranychus Test

OP-Resistant/Dip Treatment

Solvent: 7 parts by weight of dimethylformamide

Emulsifier: 2 parts by weight of alkylarylpolyglycol ether

To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are heavily infested by all stages of the greenhouse red spider mite (*Tetranychus urticae*) are dipped into a preparation of active compound of the desired concentration.

After the desired period of time, the activity in % is determined. 100% means that all spider mites have been killed; 0% means that none of the spider mites have been killed.

In this test, for example, the following compound of the Preparation Examples shows an efficacy which is superior to the prior art:

TABLE J plant-damaging mites
Tetranychus Test (OP-resistant/dip treatment)

| Active compounds | Concentration of active compound in ppm | Kill rate in % after $7^d$ |
|---|---|---|
| Example I-1-c-32 known from WO 98/05638 | 10 | 30 |
| Example I-c-4 according to the invention | 4 | 40 |

Example K

Critical Concentration Test/Soil Insects—Treatment of Transgenic Plants

Test insect: *Diabrotica balteata*—Larvae in soil

Solvent: 7 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

The preparation of active compound is poured into the soil. The concentration of the active compound in the preparation is virtually immaterial, only the amount by weight of active compound per volume unit of soil, which is stated in ppm (mg/l), matters. The soil is filled into 0.25 l pots and these are left to stand at 20° C.

Immediately after the preparation, 5 pregerminated maize corns of the cultivar YIELD GUARD (trademark of Monsanto Comp., USA) are placed into each pot. After 2 days, the corresponding test insects are placed into the treated soil. After a further 7 days, the efficacy of the active compound is determined by counting the number of maize plants that have emerged (1 plant=20% activity).

Example L

*Heliothis virescens*—Test—Treatment of Transgenic Plants

Solvent: 7 parts by weight of acetone

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Soybean shoots (*Glycine max*) of the cultivar Roundup Ready (trademark of Monsanto Comp. USA) are treated by being dipped into the preparation of active compound of the desired concentration and are populated with the tobacco budworm caterpillar *Heliothis virescens* whilst the leaves are still moist.

After the desired period of time, the kill of the insects is determined.

The invention claimed is:

1. A compound of formula (I)

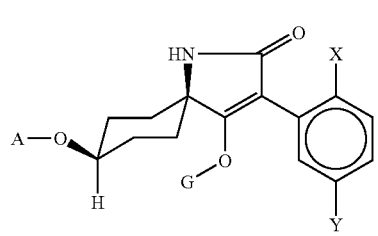

in which
X represents alkyl or halogen,
Y represents alkyl or halogen,
A represents $C_1$-$C_6$-alkyl, G represents hydrogen (a) or represents one of the groups

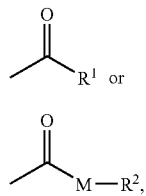

in which
M represents oxygen,
$R^1$ represents $C_1$-$C_{20}$-alkyl or $C_3$-$C_8$-cycloalkyl and
$R^2$ represents $C_1$-$C_{20}$-alkyl or benzyl.

2. A compound of formula (I) according to claim 1 in which
(a) X is $CH_3$, Y is $CH_3$, A is $CH_3$, and G is H;
(b) X is Br, Y is $CH_3$, A is $CH_3$, and G is H;
(c) X is $CH_3$, Y is $CH_3$, A is $CH_3$, and G is

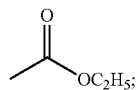

(d) X is Br, Y is $CH_3$, A is $CH_3$, and G is

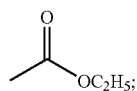

(e) X is $CH_3$, Y is Br, A is $CH_3$, and G is

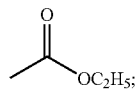

(f) X is Br, Y is $CH_3$, A is $CH_3$, and G is

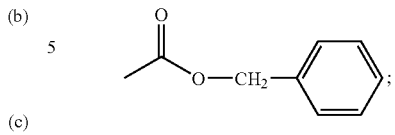

(g) X is Br, Y is $CH_3$, A is $CH_3$, and G is

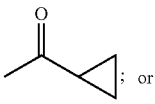

(h) X is Cl, Y is $CH_3$, A is $C_2H_5$, and G is

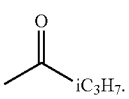

3. A pesticide comprising one or more compounds of formula (I) according to claim 1 and one or more extenders and/or surfactants.

4. A method for controlling animal pests comprising allowing an effective amount of one or more compounds of formula (I) according to claim 1 to act on pests and/or their habitat.

5. A compound of formula (I) according to claim 1 in which X is $CH_3$, Y is $CH_3$, A is $CH_3$, and G is

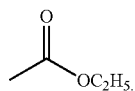

* * * * *